United States Patent [19]

Gayer et al.

[11] Patent Number: 4,628,060
[45] Date of Patent: Dec. 9, 1986

[54] FUNGICIDAL TETRAHYDROTHIOPYRAN-3,5-DIONE DERIVATIVES, INTERMEDIATE DERIVATIVES, COMPOSITIONS, AND METHOD OF USE THEREFOR

[75] Inventors: Herbert Gayer, Monheim; Wolfgang Krämer, Wuppertal; Wilhelm Brandes, Leichlingen; Gerd Hänssler; Paul Reinecke, both of Leverkusen, all of Fed. Rep. of Germany

[73] Assignee: Bayer Aktiengesellschaft, Leverkusen, Fed. Rep. of Germany

[21] Appl. No.: 606,316

[22] Filed: May 2, 1984

[30] Foreign Application Priority Data

May 21, 1983 [DE] Fed. Rep. of Germany ....... 3318648

[51] Int. Cl.⁴ .................... A61K 31/38; C07D 335/02
[52] U.S. Cl. ...................................... 514/432; 549/28
[58] Field of Search ........................... 549/28; 514/432

[56] References Cited

U.S. PATENT DOCUMENTS 3,833,610 9/1974 Hardtmann .......................... 549/28

OTHER PUBLICATIONS

Chemical Abstracts, vol. 87, 1977, p. 580, Pyrans and Thiopyrans.
Agricultural Chemistry, J5-C, p. 3, NPS, Abstract of Japanese Patent Application 52-046078.

*Primary Examiner*—Henry R. Jiles
*Assistant Examiner*—J. G. Mullins
*Attorney, Agent, or Firm*—Sprung Horn Kramer & Woods

[57] ABSTRACT

Novel substituted tetrahydrothiopyran-3,5-dione-4-carboxamide fungicides of the formula

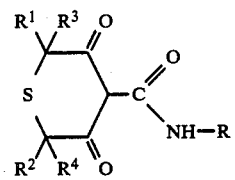

in which
R is alkyl, cycloalkyl, optionally substituted aralkyl or optionally substituted aryl,
$R^1$, $R^2$ and $R^3$ each independently is hydrogen or alkyl, and
$R^4$ is alkyl,
excepting the compounds in which
$R^1$ and $R^3$ are hydrogen
$R^4$ is methyl,
R is alkyl, phenyl or phenyl which is substituted by halogen and/or methyl, and
$R^2$ is hydrogen, or methyl.

Many of the intermediates are also new.

16 Claims, No Drawings

FUNGICIDAL TETRAHYDROTHIOPYRAN-3,5-DIONE DERIVATIVES, INTERMEDIATE DERIVATIVES, COMPOSITIONS, AND METHOD OF USE THEREFOR

The invention relates to new substituted tetrahydrothiopyran-3,5-dione-4-carboxamides, a process for their preparation and their use as agents for combating pests.

It is already known that some tetrahydrothiopyran-3,5-dione-4-carboxamides which are known as insecticides, such as, for example, tetrahydrothiopyran-3,5-dione-4-[N-(3,4-dichlorophenyl)]carboxamide have fungicidal side effects (compare Japanese Pat. No. 77 46 078 dated Apr. 12, 1977).

In addition, a fungicidal and bactericidal effect of unsubstituted tetrahydrothiopyran-3-5-dione-4-carboxamides, such as, for example, tetrahydrothiopyran-3,5-dione-4-(N-phenyl)carboxamide, is known in the pharmaceutical sector (compare U.S. Pat. No. 3,833,610).

In addition, it is known that organic sulphur compounds, such as, for example, zinc ethylene-1,2-bis-dithiocarbamate, have fungicidal properties (compare R. Wegler, 'Chemie der Pflanzenschutz- und Schädlingsbekämpfungsmttel' (Chemistry of Plant Protection Agents and Agents for Combating Pests) Volume 2, page 65, Springer Verlag, Berlin, Heidelberg, New York 1970).

However, the effect of these compounds is not always completely satisfactory, especially when low amounts and concentrations are applied.

New substituted tetrahydrothiopyran-3,5-dione-4-carboxamides have been found of the general formula (I)

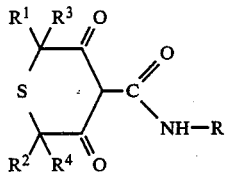

in which
R represents alkyl, cycloalkyl, optionally substituted aralkyl or optionally substituted aryl,
$R^1$, $R^2$ and $R^3$, independently of one another, represent hydrogen or alkyl, and
$R^4$ represents alkyl,
excepting compounds in which
$R^1$ and $R^3$ represent hydrogen,
$R^4$ represents methyl,
R represents alkyl, phenyl or phenyl which is substituted by halogen and/or methyl, and
$R^2$ represents methyl or hydrogen.

The compounds of the formula (I) exist in tautomeric equilibrium with compounds of the formula (Ia) and (Ib):

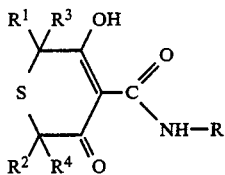

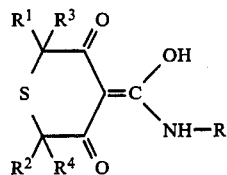

in which
R, $R^1$, $R^2$, $R^3$ and $R^4$ have the meaning indicated above.

The enol forms (Ia) and (Ib) are particularly stabilized by strong intramolecular bridging hydrogen bonds.

In addition, the compounds of the formula (I) can exist as geometric isomers or mixtures of isomers of varying composition. Both the pure isomers and the mixtures of isomers, as well as the various tautomeric structures, are claimed according to the invention.

In addition, it has been found that the new substituted tetrahydrothiopyran-3,5-dione-4-carboxamides of the general formula (I)

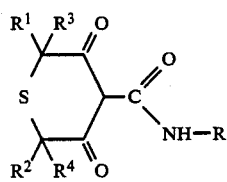

in which
R represents alkyl, cycloalkyl, optionally substituted aralkyl or optionally substituted aryl,
$R^1$, $R^2$ and $R^3$, independently of one another, represent hydrogen or alkyl, and
$R^4$ represent alkyl,
excepting the compounds in which
$R^1$ and $R^3$ represent hydrogen,
$R^2$ and $R^4$ represent methyl, and
R represents alkyl, phenyl or phenyl which is substituted by halogen and/or methyl, or
$R^1$, $R^2$ and $R^3$ represent hydrogen,
$R^4$ represents methyl, and
R represents alkyl, phenyl or phenyl which is substituted by halogen and/or methyl,
are obtained by reacting, optionally in the presence of a diluent and optionally in the presence of a base, tetrahydrothiopyran-3,5-diones of the general formula (II)

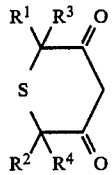

in which
$R^1$, $R^2$, $R^3$ and $R^4$ have the meaning indicated above, with isocyanates of the general formula (III)

R—N=C=O     (III)

in which
R has the meaning indicated above.

The new substituted tetrahydrothiopyran-3,5-dione-4-carboxamides of the general formula (I) have potent fungicidal properties. In this context, the compounds of the formula (I) according to the invention surprisingly show a better fungicidal efficacy than the compounds known from the state of the art, tetrahydrothiopyran-3,5-dione-4-[N-(3,4-dichlorophenyl)]carboxamide or zinc ethylene-1,2-bisdithiocarbamate, which are compounds which are related chemically and in respect of action.

Thus, the substances according to the invention represent an enrichment of technology.

The substituted tetrahydrothiopyran-3,5-dione-4-carboxamides according to the invention are generally defined by formula (I).

Those compounds of the formula (I) in which R represents straight-chain or branched alkyl having up to 8 carbon atoms, cycloalkyl having 3 to 7 carbon atoms, aralkyl which is optionally monosubstituted or polysubstituted, identically or differently, and has 1 or 2 carbon atoms in the alkyl moiety and 6 to 10 carbon atoms in the aryl moiety, and aryl which is optionally monosubstituted or polysubstituted, identically or differently, and has 6 to 10 carbon atoms, suitable aryl substituents in each case being: halogen, cyano, nitro, straight-chain or branched alkyl, alkoxy and alkylthio, each having up to 4 carbon atoms, halogenoalkyl, halogenoalkoxy and halogenoalkylthio, each having 1 or 2 carbon atoms and up to 5 identical or different halogen atoms, dioxyalkylene which is optionally monosubstituted or polysubstituted, identically or differently, by halogen or lower alkyl and has 1 or 2 carbon atom in the alkylene radical, phenoxy which is optionally monosubstituted or polysubstituted, identically or differently, by halogen, lower alkyl and lower halogenoalkyl, and alkoxycarbonylalkyl and alkoxycarbonylalkenyl each having 1 or 2 carbon atoms in the alkoxy moiety and each having up to 2 carbon atoms in the alkyl or alkenyl moiety respectively, $R^1$, $R^2$ and $R^3$, independently of one another, represent hydrogen or straight-chain or branched alkyl having up to 6 carbon atoms, and $R^4$ represents straight-chain or branched alkyl having 1 to 6 carbon atoms, excepting the compounds in which $R^1$ and $R^3$ represent hydrogen, $R^2$ and $R^4$ represent methyl, and R represents alkyl, phenyl or phenyl which is substituted by halogen and/or methyl, or $R^1$, $R^2$ and $R^3$ represent hydrogen, $R^4$ represents methyl, and R represents alkyl, phenyl or phenyl which is substituted by halogen and/or methyl, are preferred.

Those compounds of the formula (I) in which R represents straight-chain or branched alkyl having up to 6 carbon atoms, cyclopentyl or cyclohexyl; or phenyl, benzyl or naphthyl, which are optionally monosubstituted or trisubstituted, identically or differently, suitable substituents in each case being: fluorine, chlorine, bromine, nitro, cyano, methyl, ethyl, n- and i-propyl, n-, i-, s- and t-butyl, methoxy, ethoxy, methylthio, trifluoromethyl, trifluoromethoxy, trifluoromethylthio, dioxymethylene, dioxyethylene, dioxytrifluorochloroethylene, phenoxy which is optionally monosubstituted to trisubstituted, identically or differently, by methyl, chlorine or trifluoromethyl, 2-methoxycarbonylvinyl and 2-ethoxycarbonylvinyl, $R^1$, $R^2$ and $R^3$ independently of one another, represent hydrogen, methyl, ethyl, n- and i-propyl and n-, i-, s- and t-butyl and $R^4$ represents methyl, ethyl, n- and i-propyl, n-, i-, s- and t-butyl, excepting the compounds in which $R^1$ and $R^3$ represent hydrogen, $R^2$ and $R^4$ represent methyl, and R represents alkyl, phenyl or phenyl which is substituted by halogen and/or methyl, or in which $R^1$, $R^2$ and $R^3$ represent hydrogen, $R^4$ represents methyl, and R represents alkyl, phenyl or phenyl which is substituted by halogen and/or methyl, are very particularly preferred.

Apart from the compounds mentioned in the preparation examples, the following compounds of the general formula (I) may be specifically mentioned:

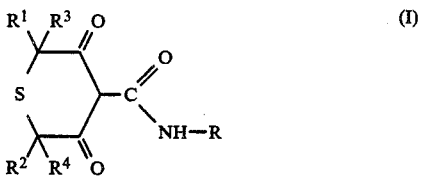

| R | $R^1$ | $R^2$ | $R^3$ | $R^4$ |
|---|---|---|---|---|
| 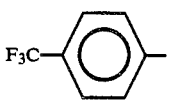 | H | H | H | $C_2H_5$ |
| 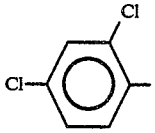 | H | H | H | $C_2H_5$ |
| 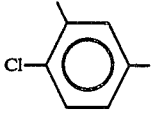 | H | H | H | $C_2H_5$ |
| 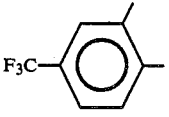 | H | H | H | $C_2H_5$ |
| 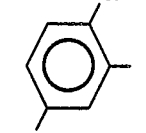 | H | H | H | $C_2H_5$ |
| 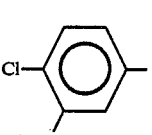 | H | H | H | $C_2H_5$ |
| 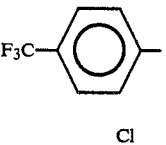 | H | H | H | $CH_3-(CH_2)_2-$ |
| 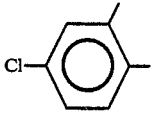 | H | H | H | $CH_3-(CH_2)_2-$ |

-continued $$\begin{array}{c} R^1 \quad R^3 \quad O \\ \diagdown \diagup \quad \parallel \\ \text{(ring with S)} \quad C \\ \diagup \diagdown \quad \diagdown \\ R^2 \quad R^4 \quad NH-R \\ \parallel \\ O \end{array}$$ (I)

| R | R¹ | R² | R³ | R⁴ |
|---|----|----|----|----|
| 3,4-dichlorophenyl | H | H | H | $CH_3-(CH_2)_2-$ |
| 3-trifluoromethyl-4-chlorophenyl | H | H | H | $CH_3-(CH_2)_2-$ |
| 3-chloro-5-trifluoromethylphenyl | H | H | H | $CH_3-(CH_2)_2-$ |
| 4-chloro-3-trifluoromethylphenyl | H | H | H | $CH_3-(CH_2)_2-$ |
| 4-chlorophenyl | H | H | H | $CH_3(CH_2)_3-$ |
| 3-trifluoromethylphenyl | H | H | H | $CH_3(CH_2)_3-$ |
| 4-trifluoromethylphenyl | H | H | H | $CH_3(CH_2)_3-$ |
| 3,4-dichlorophenyl | H | H | H | $CH_3(CH_2)_3-$ |
| 4-chlorophenyl | H | H | H | $(CH_3)_2CH-CH_2-$ |
| 3-trifluoromethylphenyl | H | H | H | $(CH_3)_2CH-CH_2-$ |
| 4-trifluoromethylphenyl | H | H | H | $(CH_3)_2CH-CH_2-$ |
| 3,4-dichlorophenyl | H | H | H | $(CH_3)_2CH-CH_2-$ |
| 4-chlorophenyl | H | $CH_3$ | H | $C_2H_5$ |
| 3-trifluoromethylphenyl | H | $CH_3$ | H | $C_2H_5$ |
| 4-trifluoromethylphenyl | H | $CH_3$ | H | $C_2H_5$ |
| 3,4-dichlorophenyl | H | $CH_3$ | H | $C_2H_5$ |
| phenyl | H | H | H | $C_2H_5$ |
| 4-methylphenyl | H | H | H | $C_2H_5$ |
| phenyl | H | H | H | $CH_3(CH_2)_2-$ |
| 4-methylphenyl | H | H | H | $CH_3(CH_2)_2-$ |
| phenyl | H | H | H | $CH_3(CH_2)_3-$ |

-continued (I)

| R | R¹ | R² | R³ | R⁴ |
|---|----|----|----|----|
| CH₃-⟨phenyl⟩- | H | H | H | CH₃(CH₂)₃— |
| ⟨phenyl⟩- | H | H | H | CH₃\\CHCH₂—/CH₃ |
| CH₃-⟨phenyl⟩- | H | H | H | CH₃\\CHCH₂—/CH₃ |
| ⟨phenyl⟩- | H | CH₃ | H | C₂H₅ |
| CH₃-⟨phenyl⟩- | H | CH₃ | H | C₂H₅ |

When, for example, 2,6-dimethyltetrahydrothiopyran-3,5-dione and phenyl isocyanate are used as starting materials, then the course of the reaction in the process according to the invention can be represented by the following diagram:

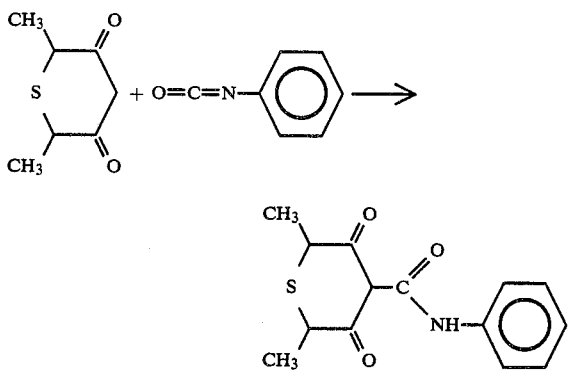

The tetrahydrothiopyran-3,5-diones which are necessary as starting materials for carrying out the process according to the invention are generally defined by formula (II). Some of the tetrahydrothiopyran-3,5-diones of the formula (II) are known [compare J. Amer. Chem. Soc. 97, 2718-2742 (1975)]. The unknown representatives in which $R^1$, $R^2$ and $R^3$ each independently is hydrogen or alkyl, and
$R^4$ is alkyl,
excepting the compounds in which $R^1$ and $R^3$ are hydrogen,
$R^4$ is methyl or i-propyl, and
$R^2$ is hydrogen or methyl, can be prepared in an analogous manner by reacting, optionally in the presence of a diluent, such as, for example, methanol, and optionally in the presence of a base, such as, for example, sodium methylate, at temperatures between −20° C. and +50° C., α-halogenoketones of the formula (IV)

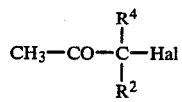

in which
$R^2$ and $R^4$ have the meaning indicated above, and
Hal represents chlorine or bromine,
with α-mercaptocarboxylic esters of the formula (V)

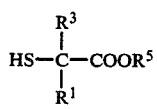

in which
$R^1$ and $R^3$ have the meaning indicated above, and
$R^5$ represents straight-chain or branched alkyl having up to 4 carbon atoms,
to give the esters of the formula (VI)

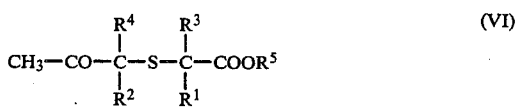

in which
$R^1$, $R^2$, $R^3$, $R^4$ and $R^5$ have the meaning indicated above,
and cyclizing the latter in a 2nd stage, optionally in the presence of a diluent, such as, for example, toluene, and optionally in the presence of a base, such as, for example, sodium methylate, to give the tetrahydrothiopyran-3,5-diones of the formula (II).

The isocyanates which are also necessary as starting materials for carrying out the process according to the invention are generally defined by formula (III).

Isocyanates of the formula (III), α-halogenoketones of the formula (IV) and α-mercaptocarboxylic esters of the formula (V) are generally-known compounds in organic chemistry.

Suitable diluents for the process according to the invention are inert organic solvents. These preferably include aliphatic and aromatic hydrocarbons, which are optionally chlorinated, such as petrol, benzene, toluene, xylene, methylene chloride, chloroform, carbon tetrachloride, chlorobenzene and dichlorobenzene, ethers, such as diethyl ether, diisopropyl ether, dioxane and tetrahydrofuran, ketones, such as acetone, butanone and methyl isopropyl ketone, nitriles, such as acetonitrile and propionitrile and the highly polar solvents dimethyl sulphoxide and hexamethylphosphoric triamide.

The reaction according to the invention can optionally be carried out in the presence of a base. Tertiary organic nitrogen bases, such as triethylamine, N,N-dimethylbenzylamine, N,N-dimethylaniline, diazabicyclononene (DBN) or diazabicycloundecene (DBU) are preferably used.

The reaction temperatures in the process according to the invention can be varied within a wide range. In general, it is carried out at temperatures between $-10°$ C. and $+100°$ C., preferably at temperatures between $+10°$ C. and $+80°$ C.

In order to carry out the process according to the invention, generally 1.0 to 1.2 mols, preferably equimolar amounts, of isocyanate of the formula (III) and optionally 1.0 to 1.2 mols, preferably equimolar amounts, of base are employed per mol of tetrahydrothiopyran-3,5-dione of the formula (II). After a reaction time of one to two hours at the required temperature, the mixture is allowed to reach room temperature and the base is removed by extraction with water and the diluent by distillation in vacuo.

In order to isolate and purify the compounds of the formula (I), the oily residue from distillation is chromatographed on a silica gel column using an eluant mixture of ether, petroleum ether and acetic acid. The compounds of the formula (I) purified in this manner exist either as oils or as crystalline solids which can be recrystallized from ethanol. The melting point or $^1$H-NMR spectrums serve for characterization.

The active compounds according to the invention exhibit a powerful microbicidal action and can be employed in practice for combating undesired microorganisms. The active compounds are suitable for use as plant protection agents, especially as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating cereal diseases, such as, for example, against the snow mould on rye causative organism (*Fusarium nivale*) or against the brown rust on wheat causative organism (*Puccinia recondita*), for combating fruit diseases and vegetable diseases, such as, for example, against the apple scab causative organism (*Venturia inaequalis*) or against the late blight of tomato causative organism (*Phytophtora infestans*), or for combating rice diseases, such as, for example, against the blast disease of rice causative organism (*Pyricularia oryzae*). Furthermore, the good action against *Cochliobolus sativus* and *Pyrenophora teres* on cereals should be mentioned.

The active compounds according to the invention exhibit both protective and systemic activity, and can also be used successfully as seed-dressing agents.

In addition, the active compounds according to the invention also possess insecticidal and acaricidial activity.

The active compounds can be converted to the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and-/or dispersing agents, and/or form-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumen hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g are generally required.

For the treatment of soil, active compound concentrations of 0.00001 to 0.1% by weight, preferably 0.001 to 0.02% by weight are required at the place of action.

PREPARATING EXAMPLES

Example 1

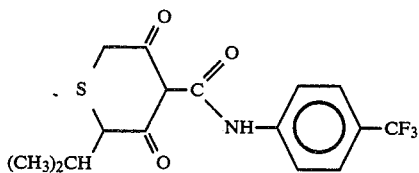

First 124 g (1 mol) of diazabicycloundecene (DBU) and then 188 g (1 mol) of 4-trifluoromethylphenyl isocyanate are added dropwise, at 25° C. with stirring, to 172 g (1 mol) of 2-isopropyltetrahydrothiopyran-3,5-dione in 1 liter of tetrahydrofuran. After addition is complete, the mixture is stirred at room temperature for one hour, then washed several times with aqueous 2N hydrochloric acid and the solvent is removed in vacuo. The oily residue is purified by chromatography on silica gel (eluant: ether/petroleum ether/glacial acetic acid in the ratio 10:10:0.3). 190 g (53% of theory of 2-isopropyl-tetrahydrothiopyran-3,5-dione-4-[N-(4-trifluoromethyl-phenyl)]carboxamide of melting point 121° C. are obtained.

Preparation of the starting compound:

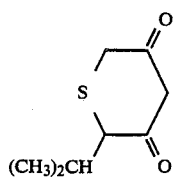
(a)

204 g (1 mol) of 3-methoxycarbonylmethylthio-4-methyl-2-pentanone are added dropwise within one hour, at 0° C. with vigorous stirring, to a suspension of 108 g (2 mol) of freshly prepared sodium methylate in 2 liters of absolute toluene. The reaction mixture is stirred at 0° C. for a further 30 minutes, then poured into a mixture of 200 ml of concentrated hydrochloric acid and 800 ml of ice-water, and the organic phase is separated off, and the aqueous phase is extracted three times with dichloromethane. The combined organic phases are concentrated to 500 ml in vacuo and extracted with 500 ml of ice-cold 4N sodium hydroxide solution. The aqueous extracts are immediately acidified with a total of 400 ml of ice-cold hydrochloric acid and extracted three times with 200 ml of dichloromethane each time. The combined dichloromethane phases are dried over sodium sulphate and the solvent is removed in vacuo. The remaining solid is recrystallized from ligroin/ethanol. 150 g (87% of theory) of 2-isopropyltetrahydro-thiopyran-3,5-dione of melting point 71° C. are obtained.

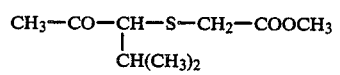
(b)

First 106 g (1 mol) of methyl mercaptoacetate and then 165 g (1 mol) of 3-bromo-3-methyl-2-butanone are added dropwise, at 0° C. with stirring, to a solution of 54 g (1 mol) of sodium methylate in 1 liter of methanol. After addition is complete, the reaction mixture is boiled to reflux for 30 minutes and, after cooling, precipitated sodium bromide is filtered off and the solvent is removed in vacuo. The residue is partitioned between a mixture of 500 ml of dichloromethane and 500 ml of water, and the organic phase is separated off, dried over sodium sulphate and the solvent is removed in vacuo. The residue is distilled under high vacuum. 122.5 g (67% of theory) of 3-methoxycarbonylmethylthio-4-methyl-2-pentanone of boiling point 80° C. at 0.4 mbar are obtained.

In a corresponding manner and in accordance with the general details of the preparation, the following compounds of the general formula (I) are obtained:

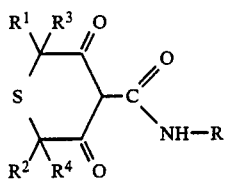
| Example No. | R | $R^1$ | $R^2$ | $R^3$ | $R^4$ | Physical properties |
|---|---|---|---|---|---|---|
| 2 | 4-Cl-C₆H₄– | H | H | H | $C_2H_5$ | M.p. 68° C. |
| 3 | 3-F₃C-C₆H₄– | H | H | H | $C_2H_5$ | ¹H—NMR: 0,8–1,4(3);1,6–2,3(2); 3,0–3,7(3);7,1–7,0(4) |
| 4 | 3-Cl-4-F₃C-C₆H₃– | H | H | H | $C_2H_5$ | M.p.: 95° C. |
| 5 | 4-Cl-C₆H₄– | H | H | H | $CH_3(CH_2)_2-$ | M.p.: 81° C. |
| 6 | 3-F₃C-C₆H₄– | H | H | H | $CH_3(CH_2)_2-$ | ¹H—NMR: 0,7–1,1(3);1,1–2,2(4); 3,1–3,6(3);7,1–8,0(4) |
| 7 | 3-Cl-4-F₃C-C₆H₃– | H | H | H | $CH_3(CH_2)_2-$ | M.p.: 82° C. |
| 8 | 3-(C₂H₅OOC—CH=CH)-C₆H₄– | H | H | H | $CH_3(CH_2)_2-$ | M.p. 62–72° C. |
| 9 | C₆H₅– | H | H | H | $(CH_3)_2CH-$ | M.p. 68–69° C. |
| 10 | 1-naphthyl | H | H | H | $(CH_3)_2CH-$ | M.p. 150° C. |

-continued
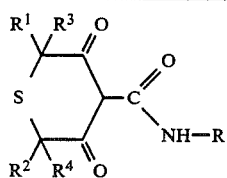
| Example No. | R | R¹ | R² | R³ | R⁴ | Physical properties |
|---|---|---|---|---|---|---|
| 11 | 2-CH₃-C₆H₄- | H | H | H | (CH₃)₂CH— | M.p. 95–97° C. |
| 12 | 3-CH₃-C₆H₄- | H | H | H | (CH₃)₂CH— | ¹H—NMR: 0,7–1,3(6);2,3s(3); 2,0–2,5(1);2,8–3,8(3); 6,7–7,4(4) |
| 13 | 4-CH₃-C₆H₄- | H | H | H | (CH₃)₂CH— | M.p. 73° C. |
| 14 | 3,4-(CH₃)₂-C₆H₃- | H | H | H | (CH₃)₂CH— | M.p. 77–79° C. |
| 15 | 4-(CH₃)₂CH-C₆H₄- | H | H | H | (CH₃)₂CH— | ¹H—NMR: 0,7–1,4(12);2,0–3,8(5); 7,0–7,5(4), |
| 16 | 4-(CH₃)₃C-C₆H₄- | H | H | H | (CH₃)₂CH— | ¹H—NMR: 1,35s(9); 0,7–1,4(6);2,1–2,8(1); 3,0–3,9(3);7,4s(4) |
| 17 | 3-F₃C-C₆H₄- | H | H | H | (CH₃)₂CH— | M.p. 62–64° C. |
| 18 | 4-C₂H₅O-C₆H₄- | H | H | H | (CH₃)₂CH— | M.p. 101° C. |
| 19 | 3-F₃CO-C₆H₄- | H | H | H | (CH₃)₂CH— | M.p. 61° C. |
| 20 | 4-F₃CO-C₆H₄- | H | H | H | (CH₃)₂CH— | M.p. 65–66° C. |

-continued
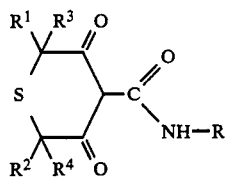
| Example No. | R | R¹ | R² | R³ | R⁴ | Physical properties |
|---|---|---|---|---|---|---|
| 21 | F₃CS—C₆H₄— | H | H | H | $(CH_3)_2CH-$ | M.p. 70° C. |
| 22 | 2-O₂N—C₆H₄— | H | H | H | $(CH_3)_2CH-$ | M.p. 75–80° C. |
| 23 | 4-O₂N—C₆H₄— | H | H | H | $(CH_3)_2CH-$ | M.p. 124° C. |
| 24 | 4-F—C₆H₄— | H | H | H | $(CH_3)_2CH-$ | M.p. 60–62° C. |
| 25 | 4-Br—C₆H₄— | H | H | H | $(CH_3)_2CH-$ | M.p. 118–119° C. |
| 26 | 4-Cl—C₆H₄— | H | H | H | $(CH_3)_2CH-$ | M.p. 111–115° C. |
| 27 | 3-Cl—C₆H₄— | H | H | H | $(CH_3)_2CH-$ | ¹H—NMR: 1,9–2,2(6); 2,1–2,7(1);2,9–3,9(3); 6,9–7,5(3);7,6–7,5s(1) |
| 28 | 3,4-Cl₂—C₆H₃— | H | H | H | $(CH_3)_2CH-$ | M.p. 89–94° C. |
| 29 | 3,5-Cl₂—C₆H₃— | H | H | H | $(CH_3)_2CH-$ | M.p. 103° C. |
| 30 | 3-Cl-4-CH₃—C₆H₃— | H | H | H | $(CH_3)_2CH-$ | M.p. 72–75° C. |

-continued
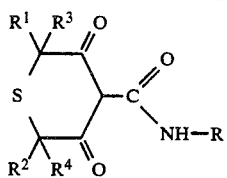
| Example No. | R | R¹ | R² | R³ | R⁴ | Physical properties |
|---|---|---|---|---|---|---|
| 31 | 2-Cl, 5-CH₃-phenyl | H | H | H | $(CH_3)_2CH-$ | M.p. 101° C. |
| 32 | 3-Cl, 4-CF₃-phenyl | H | H | H | $(CH_3)_2CH-$ | M.p. 111° C. |
| 33 | 4-Cl, 3-CF₃-phenyl | H | H | H | $(CH_3)_2CH-$ | M.p. 135° C. |
| 34 | 2-Cl, 5-CF₃-phenyl | H | H | H | $(CH_3)_2CH-$ | M.p. 171–173° C. |
| 35 | 4-Cl, 2-CF₃-phenyl | H | H | H | $(CH_3)_2CH-$ | M.p. 98° C. |
| 36 | 2-Cl, 4-OCF₃-phenyl | H | H | H | $(CH_3)_2CH-$ | M.p. 55–56° C. |
| 37 | 2-CF₃, 4-NO₂-phenyl | H | H | H | $(CH_3)_2CH-$ | ¹H—NMR: 0.9–1,4(6); 2,0–2,9(1);3,1–3,9(3); 7,9–8,3(3) |
| 38 | 2-Cl, 4-OCH₃-phenyl | H | H | H | $(CH_3)_2CH-$ | M.p. 99–102° C. |
| 39 | 3-CF₃-phenoxy-phenyl | H | H | H | $(CH_3)_2CH-$ | ¹H—NMR: 0,7–1,2(6); 2,0–2,6(1);2,7–3,7(2); 6,7–7,7(8) |

-continued

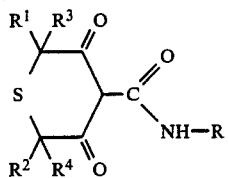

| Example No. | R | R¹ | R² | R³ | R⁴ | Physical properties |
|---|---|---|---|---|---|---|
| 40 | 4-(4-trifluoromethylphenoxy)phenyl | H | H | H | $(CH_3)_2CH-$ | $^1H$—NMR: 0,8–1,3(6); 2,0–2,6(1);2,7–3,7(3); 6,7–7,7(8) |
| 41 | 2,3-(chlorodifluoromethylenedioxy)phenyl | H | H | H | $(CH_3)_2CH-$ | $^1H$—NMR: 0,8–1,3(6); 2,1–2,6(1);2,9–3,6(2); 6,9–7,3(2);7,4–7,6(1) |
| 42 | $CH_3$ | H | H | $CH_3$ | $CH_3$ | $^1H$—NMR: 1,2–1,8(6); 2,95d(3);3,2–4,1(2) |
| 43 | $(CH_3)_2CH-$ | H | H | $CH_3$ | $CH_3$ | $^1H$—NMR: 1,0–1,8(12); 3,3–4,4(3) |
| 44 | $CH_3(CH_2)_3-$ | H | H | $CH_3$ | $CH_3$ | $^1H$—NMR: 0,8–1,15(3); 1,15–1,8(10);3,1–4,0(4) |
| 45 | $(CH_3)_2CH-CH_2-$ | H | H | $CH_3$ | $CH_3$ | $^1H$—NMR: 0,8–1,1(6); 1,2–1,9(7);2,8–4,0(4) |
| 46 | $(CH_3)_3C-$ | H | H | $CH_3$ | $CH_3$ | $^1H$—NMR: 1,4s(9);1,2–1,8 (6);3,2–4,0(2) |
| 47 | cyclohexyl | H | H | $CH_3$ | $CH_3$ | $^1H$—NMR: 1,0–2,2(16); 32,–4,0(3) |
| 48 | benzyl ($C_6H_5-CH_2-$) | H | H | $CH_3$ | $CH_3$ | $^1H$—NMR: 1,2–1,9(6); 3,3–4,1(2);4,6d(2); 7,4s(5) |
| 49 | phenyl | H | H | $CH_3$ | $CH_3$ | M.p. 155° C. |
| 50 | naphthyl | H | H | $CH_3$ | $CH_3$ | M.p. 87–94° C. |
| 51 | 2-methylphenyl | H | H | $CH_3$ | $CH_3$ | M.p. 154° C. |
| 52 | 3-methylphenyl | H | H | $CH_3$ | $CH_3$ | M.p. 72–74° C. |

-continued
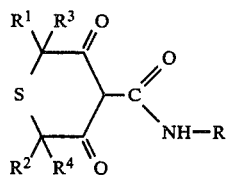
| Example No. | R | R¹ | R² | R³ | R⁴ | Physical properties |
|---|---|---|---|---|---|---|
| 53 | CH₃—C₆H₄— | H | H | CH₃ | CH₃ | M.p. 70° C. |
| 54 | (CH₃)₂CH—C₆H₄— | H | H | CH₃ | CH₃ | ¹H—NMR: 1–1,8(12); 2,5–3,1(1);3,4–3,9(2); 7,0–7,6(4) |
| 55 | (CH₃)₃C—C₆H₄— | H | H | CH₃ | CH₃ | M.p. 90–92° C. |
| 56 | 3,4-(CH₃)₂—C₆H₃— | H | H | CH₃ | CH₃ | ¹H—NMR: 1,0–1,8; 2,2s(6);3,2–3,9(2); 6,8–7,5(3) |
| 57 | C₂H₅O—C₆H₄— | H | H | CH₃ | CH₃ | M.p. 114–117° C. |
| 58 | 3-F₃C—C₆H₄— | H | H | CH₃ | CH₃ | M.p. 82–87° C. |
| 59 | 4-F₃C—C₆H₄— | H | H | CH₃ | CH₃ | ¹H—NMR: 1,2–1,9(6); 3,3–3,9(2);7,7s(4); |
| 60 | 3-F₃CO—C₆H₄— | H | H | CH₃ | CH₃ | M.p. 90–93° C. |
| 61 | 4-F₃CO—C₆H₄— | H | H | CH₃ | CH₃ | M.p. 75–80° C. |
| 62 | 4-F₃CS—C₆H₄— | H | H | CH₃ | CH₃ | M.p. 60° C. |

-continued
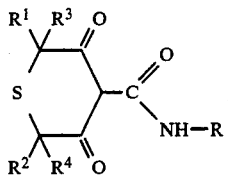
| Example No. | R | $R^1$ | $R^2$ | $R^3$ | $R^4$ | Physical properties |
|---|---|---|---|---|---|---|
| 63 | 2-NO₂-phenyl | H | H | CH₃ | CH₃ | ¹H—NMR: 1,2–1,8(6); 3,2–3,9(2);7,4–8,2(3); 8.4–8,6(1) |
| 64 | 3-O₂N-phenyl | H | H | CH₃ | CH₃ | M.p. 158–160° C. |
| 65 | 4-O₂N-phenyl | H | H | CH₃ | CH₃ | M.p. 65–70° C. |
| 66 | 4-F-phenyl | H | H | CH₃ | CH₃ | M.p. 90–95° C. |
| 67 | 4-Br-phenyl | H | H | CH₃ | CH₃ | M.p. 77–79° C. |
| 68 | 3-Cl-phenyl | H | H | CH₃ | CH₃ | ¹H—NMR: 1,1–1,9(6); 3,4–4,3(2);7,0–7,5(3); 7,55–7,8(1) |
| 69 | 4-Cl-phenyl | H | H | CH₃ | CH₃ | M.p. 97–98° C. |
| 70 | 3,4-di-Cl-phenyl | H | H | CH₃ | CH₃ | M.p. 88–90° C. |
| 71 | 2,4-di-Cl-phenyl | H | H | CH₃ | CH₃ | M.p. 105–108° C. |
| 72 | 3,5-di-Cl-phenyl | H | H | CH₃ | CH₃ | M.p. 113–115° C. |

-continued
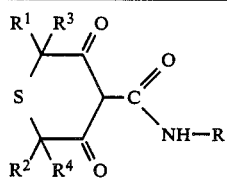
| Example No. | R | $R^1$ | $R^2$ | $R^3$ | $R^4$ | Physical properties |
|---|---|---|---|---|---|---|
| 73 | 2-Cl, 3-CH₃-phenyl | H | H | CH₃ | CH₃ | ¹H—NMR: 1,0–1,8(6); 2,3s(3);3,2–4,1(2); 7,1–7,5(3) |
| 74 | 2-CH₃, 3-Cl-phenyl | H | H | CH₃ | CH₃ | M.p. 102–104° C. |
| 75 | 2-OCH₃, 3-Cl-phenyl | H | H | CH₃ | CH₃ | M.p. 93–95° C. |
| 76 | 2-Cl, 4-CF₃-phenyl | H | H | CH₃ | CH₃ | M.p. 78–80° C. |
| 77 | 2-Cl, 5-CF₃-phenyl | H | H | CH₃ | CH₃ | ¹H—NMR: 1,3–1,8(6); 3,4–4,3(2);7,2–7,7(2); 8,5–8,7(1) |
| 78 | 2-Cl, 5-CF₃-phenyl (alt) | H | H | CH₃ | CH₃ | M.p. 104–106° C. |
| 79 | 2-CF₃, 5-Cl-phenyl | H | H | CH₃ | CH₃ | ¹H—NMR: 1,1–1,9(6); 3,4–4,3(2);7,5–7,7s(2);7,75–8,0(1) |
| 80 | 2-Cl, 4-OCF₃-phenyl | H | H | CH₃ | CH₃ | M.p. 79–86° C. |
| 81 | 2-CF₃, 4-NO₂-phenyl | H | H | CH₃ | CH₃ | M.p. 79–80° C. |

-continued

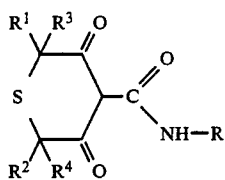

| Example No. | R | $R^1$ | $R^2$ | $R^3$ | $R^4$ | Physical properties |
|---|---|---|---|---|---|---|
| 82 | $C_2H_5OOC-CH=CH-$(phenyl) | H | H | $CH_3$ | $CH_3$ | $^1$H—NMR: 1,0–2,0(9); 3,2–4,0(2);4,0–4,6q(2); 6,2–6,6(1);7,1–7,9(5) |
| 83 | (benzodioxole-CF$_2$Cl) | H | H | $CH_3$ | $CH_3$ | $^1$H—NMR: 1,0–1,9(6); 3,3–3,9(2);7,0–7,8(3) |
| 84 | 3-CF$_3$-phenoxy-phenyl | H | H | $CH_3$ | $CH_3$ | $^1$H—NMR: 1,2–1,9(6); 3,3–4,2(2);6,8–7,8(8) |
| 85 | 4-CF$_3$-phenoxy-phenyl | H | H | $CH_3$ | $CH_3$ | $^1$H—NMR: 1,0–1,6(6); 3,2–3,9(2);6,7–7,7(8); |
| 86 | phenyl | H | $CH_3$ | $CH_3$ | $CH_3$ | M.p. 61–62° C. |
| 87 | 2-CH$_3$-phenyl | H | $CH_3$ | $CH_3$ | $CH_3$ | M.p. 69–72° C. |
| 88 | 3-CH$_3$-phenyl | H | $CH_3$ | $CH_3$ | $CH_3$ | $^1$H—NMR: 1,2–1,8(9); 2,3s(3);3,5–4,1(1); 7,0–7,6(4) |
| 89 | 4-CH$_3$-phenyl | H | $CH_3$ | $CH_3$ | $CH_3$ | $^1$H—NMR: 1,4–1,9(9); 2,35s(3);3,5–4,2(1); 6,8–7,5(4) |
| 90 | 2,4-(CH$_3$)$_2$-phenyl | H | $CH_3$ | $CH_3$ | $CH_3$ | $^1$H—NMR: 1,2–1,8(9); 2,2s(6);3,5–4,2(1); 6,9–7,4(3) |

-continued
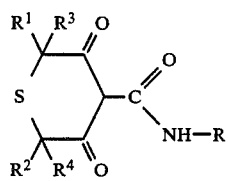
| Example No. | R | R¹ | R² | R³ | R⁴ | Physical properties |
|---|---|---|---|---|---|---|
| 91 | (CH₃)₂CH—C₆H₄— | H | CH₃ | CH₃ | CH₃ | $^1$H—NMR: 1,0–1,8(15); 2,5–3,0(1);3,5–4,0 (1);6,9–7,5(4) |
| 92 | (CH₃)₃C—C₆H₄— | H | CH₃ | CH₃ | CH₃ | $^1$H—NMR: 1,0–1,8(18); 3,5–4,0(1);7,2–7,5(4); |
| 93 | F₃C—C₆H₄— (meta) | H | CH₃ | CH₃ | CH₃ | $^1$H—NMR: 1,0–1,8(9); 3,5–4,0(1);7,2–7,9(4) |
| 94 | F₃C—C₆H₄— (para) | H | CH₃ | CH₃ | CH₃ | $^1$H—NMR: 1,0–1,8(9); 3,5–4,1(1);7,6(4) |
| 95 | Cl—C₆H₄— | H | CH₃ | CH₃ | CH₃ | M.p. 74–79° C. |
| 96 | C₆H₅— | H | H | (CH₃)₂CH— | (CH₃)₂CH— | M.p. 59–65° C. |
| 97 | Cl—C₆H₄— | H | H | (CH₃)₂CH— | (CH₃)₂CH— | M.p. 102–120° C. |
| 98 | Cl,Cl—C₆H₃— | H | H | (CH₃)₂CH— | (CH₃)₂CH— | M.p. 91–98° C. |
| 99 | Cl—C₆H₄— | H | H | CH₃ | (CH₃)₂CH— | M.p. 95–104° C. |
| 100 | Cl,Cl—C₆H₃— | H | H | CH₃ | (CH₃)₂CH— | $^1$H—NMR: 0,8–1,8(9); 2,0–2,9(1);3,0–4,0(2); 7,4(2);7,8(1); |

-continued
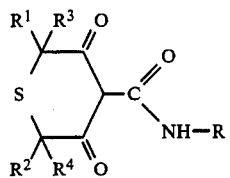
| Example No. | R | R¹ | R² | R³ | R⁴ | Physical properties |
|---|---|---|---|---|---|---|
| 101 | 4-F₃C-C₆H₄- | H | H | CH₃ | (CH₃)₂CH— | ¹H—NMR: 0,8–1,2(6); 1,2–3,7(3);2,0–2,9(1); 2,9–4,0(2);7,1–7,9(4) |
| 102 | 4-F₃C-C₆H₄- | H | CH₃ | H | CH₃ | M.p. 81–82° C. |
| 103 | 4-Cl-C₆H₄- | H | CH₃ | CH₃ | CH₃ | ¹H—NMR: 1,2–1,9(9); 3,6–4,3(1);7,2–7,7(4) |
| 104 | 3,4-Cl₂-C₆H₃- | H | CH₃ | CH₃ | CH₃ | ¹H—NMR: 1,2–1,9(9); 3,6–4,2(1);7,45(2); 7,85(1) |
| 105 | 4-F-C₆H₄- | H | CH₃ | CH₃ | CH₃ | ¹H—NMR: 1,3–1,9(9); 3,6–4,3(1);6,8–7,8(4); |
| 106 | 3-Cl-4-CH₃-C₆H₃- | H | CH₃ | CH₃ | CH₃ | ¹H—NMR: 1,3–1,9(9); 2,9(3);3,4–4,3(1); 7,2–7,4(2);7,75(1) |
| 107 | 2,4-Cl₂-5-CF₃-C₆H₂- | H | CH₃ | CH₃ | CH₃ | ¹H—NMR: 1,1–1,9(9); 3,5–4,3(1);7,7(2) |
| 108 | 2-Cl-4-CF₃-C₆H₃- | H | CH₃ | CH₃ | CH₃ | ¹H—NMR: 1,3–1,9(9); 3,5–4,3(1);7,4–7,75(2); 7,75–8,0(1) |
| 109 | 3-Cl-4-CF₃-C₆H₃- | H | CH₃ | CH₃ | CH₃ | ¹H—NMR: 1,3–1,9(9); 3,5–4,3(1);7,4–7,9(2); 8,4–8,7(1) |

-continued

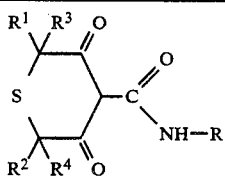

| Example No. | R | $R^1$ | $R^2$ | $R^3$ | $R^4$ | Physical properties |
|---|---|---|---|---|---|---|
| 110 | 2-Cl, 4-CF₃-phenyl | H | CH₃ | CH₃ | CH₃ | M.p. 91–92° C. |
| 111 | 3-Cl, 4-CF₃-phenyl | H | CH₃ | CH₃ | CH₃ | ¹H—NMR: 1,3–1,9(9); 3,5–4,3(1);7,2–8,1(3) |
| 112 | 4-(CH₃CH₂O)-phenyl | H | CH₃ | CH₃ | CH₃ | M.p. 68–69° C. |
| 113 | 3-CF₃O-phenyl | H | CH₃ | CH₃ | CH₃ | ¹H—NMR: 1,3–1,9(9); 3,6–4,3(1);7,0–8,0(4) |
| 114 | 4-CF₃O-phenyl | H | CH₃ | CH₃ | CH₃ | ¹H—NMR: 1,3–1,9(9), 3,6–4,3(1);7,1–8,8(4) |
| 115 | 4-(3-CF₃-phenoxy)-phenyl | H | CH₃ | CH₃ | CH₃ | ¹H—NMR: 1,3–1,9(9); 3,6–4,3(1);6,9–7,8(8) |
| 116 | 4-(4-CF₃-phenoxy)-phenyl | H | CH₃ | CH₃ | CH₃ | ¹H—NMR: 1,3–1,9(9); 3,6–4,3(1);6,8–7,8(8) |
| 117 | 3-Cl, 4-CF₃O-phenyl | H | CH₃ | CH₃ | CH₃ | ¹H—NMR: 1,3–1,9(9); 3,6–4,3(1);7,2–7,7(2); 7,9(1) |
| 118 | 3-CF₃-phenyl | H | H | H | CH₃ | M.p. 72–75° C. |
| 119 | 4-CF₃-phenyl | H | H | H | CH₃ | M.p. 75–78° C. |

-continued

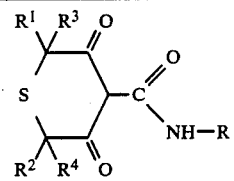

| Example No. | R | R¹ | R² | R³ | R⁴ | Physical properties |
|---|---|---|---|---|---|---|
| 120 | 3-CF₃-phenyl | H | $CH_3$ | H | $CH_3$ | M.p. 61–63° C. |
| 121 | $C_6H_5$ | H | H | H | $CH_3$ | $^1$H—NMR: 1.0–1.5m(3);1.8–2.5 m(2);3.0–4.0m(3); 7.4–8.0m(5) |
| 122 | $C_6H_5$ | H | H | H | $CH_3—(CH_2)_2—$ | $^1$H—NMR: 0.8–1.0t(3) 1.1–2.0m(4);3.0–3.5m(3); 6.9–7.5m(5) |
| 123 | $C_6H_5$ | H | H | H | $CH_3—(CH_2)_5—$ | $^1$H—NMR: 0.7–1.0t(3); 1.1–2.0m(10);3.0–3.6m (3);7.0–7.7m(5) |
| 124 | 4-Cl-phenyl | H | H | H | $CH_3—(CH_2)_5—$ | Fp 82° C. |
| 125 | 4-Cl-phenyl | H | H | H | $CH_3—(CH_2)_3—$ | Fp 71°–73° C. |
| 126 | 4-F₃CO-phenyl | H | H | H | $CH_3$ | Fp 62°–63° C. |
| 127 | 4-F₃CO-phenyl | H | H | H | $C_2H_5$ | $^1$H—NMR: 1.0–1.5m(3); 1.5–2.5m(2);3.0–4.0 m(3);7.3–8.3m(4) |
| 128 | 4-F₃CO-phenyl | H | H | H | $CH_3—(CH_2)_2—$ | NMR 0.8–1.3t(3);1.3– 2.5m(4);3.1–4.0m(3); 7.3–8.2m(4) |
| 129 | 4-F₃CO-phenyl | H | $CH_3$ | H | $CH_3$ | $^1$H—NMR 0.7–1.3m(6);3.0– 3.7m(3);7.3–8.0m(4) |

*The $^1$H—NMR data indicate the chemical shift in ppm. Unless otherwise indicated, the signal groups are multiplets, and the figure in parentheses in each case indicates the number of protons assigned.

Use examples:
In the following use examples, the compounds detailed below are used as comparison substances:

Tetrahydrothiopyran-3,5-dione-4-[N-(3,4-dichlorophenyl)]-carboxamide and

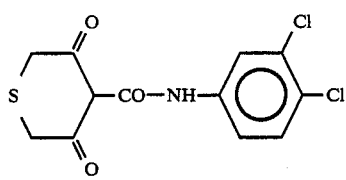
(A)

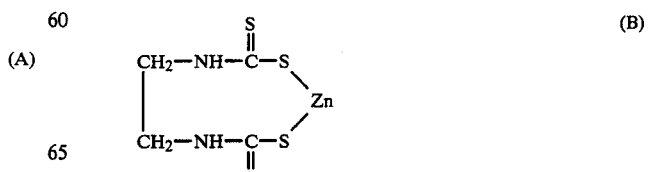
(B)

Zinc ethylene-1,2-bis-(dithiocarbamate)

EXAMPLE A

*Fusarium nivale* test (rye)/seed treatment

The active compounds are used as dry dressings. These are prepared by extending the particular active compound with a ground mineral to give a finely pulverulent mixture, which ensures uniform distribution on the seed surface.

To apply the dressing, the infected seed is shaken with the dressing in a closed glass flask for 3 minutes.

2 batches of 100 grains of the rye are sown 1 cm deep in standard soil and are cultivated in a greenhouse at a temperature of about 10° C. and a relative atmospheric humidity of 95%, in seedboxes which are exposed to light for 15 hours daily.

About 3 weeks after sowing, the plants are evaluated for symptoms of snow mould.

In this test, a clearly superior activity compared with the prior art is shown, for example, by the compounds according to the following preparation examples: 49 and 99.

EXAMPLE B

Puccinia test (wheat)/protective

Solvent: 100 parts by weight of dimethylformamide

Emulsifier: 0.25 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are inoculated with a spore suspension of *Puccinia recondita* in a 0.1% strength aqueous agar solution. After the spore suspension has dried on, the plants are sprayed with the preparation of active compound until dew-moist. The plants remain in an incubation cabinet at 20° C. and 100% relative atmospheric humidity for 24 hours.

The plants are placed in a greenhouse at a temperature of about 20° C. and a relative atmospheric humidity of about 80% in order to promote the development of rust pustules.

Evaluation is carried out 10 days after the inoculation.

In this test, a clearly superior activity compared with the prior art is shown, for example, by the compounds according to the following preparation examples: 58, 96 and 101.

EXAMPLE C

Phytophthora Test (tomato)/protective

Solvent: 4.7 parts by weight of acetone

Emulsifier: 0.3 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of *Phytophthora infestans*.

The plants are placed in an incubation cabinet at 100% relative atmospheric humidity and at about 20° C.

Evaluation is carried out 3 days after the inoculation.

In this test, a clearly superior activity compared with the prior art is shown, for example, by the compounds according to the preparation examples: 26, 28, 49, 53, 79 and 100.

EXAMPLE D

Venturia test (apple)/protective

Solvent: 4.7 parts by weight of acetone

Emulsifier: 0.3 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (*Venturia inaequalis*) and then remain in an incubation cabinet at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, a clearly superior activity compared with the prior art is shown, for example, by the compounds according to the following preparation examples: 69 and 70.

EXAMPLE E

Pyricularia test (rice)/protective

Solvent: 12.5 parts by weight of acetone

Emulsifier: 0.3 parts by weight of alkylaryl polyglycol ether

To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of *Pyricularia oryzae*. The plants are then placed in a greenhouse at 100% relative atmospheric humidity and 25° C.

Evaluation of the disease infestation is carried out 4 days after the inoculation.

In this test, a clearly superior activity compared with the prior art is shown, for example, by the compounds according to the following preparation examples: 69, 99 and 100.

EXAMPLE F

Pyricularia test (rice)/systemic

Solvent: 12.5 parts by weight of acetone

Emulsifier: 0.3 parts by weight of alkylaryl polyglycol ether

To produce a suitable preparation of active compound, 1 part by weight of active compound is mixed with the stated amount of solvent, and the concentrate is diluted with water and the stated amount of emulsifier, to the desired concentration.

To test for systemic properties, standard soil in which young rice plants have been grown is watered with 40 ml of the preparation of active compound. 7 days after the treatment, the plants are inoculated with an aqueous spore suspension of *Pyricularia oryzae.* Thereafter, the plants remain in a greenhouse at a temperature of 25° C. and a relative atmospheric humidity of 100% until they are evaluated.

Evaluation of the disease infestation is carried out 4 days after the inoculation.

In this test, a clearly superior activity compared with the prior art is shown, for example, by the compounds according to the following preparation examples: 46 and 70.

It will be understood that the specification and examples are illustrative but not limitative of the present invention and that other embodiments within the spirit and scope of the invention will suggest themselves to those skilled in the art.

We claim:

1. A substituted tetrahydrothiopyran-3,5-dione-4-carboxamide of the formula 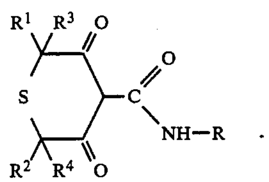 in which R is alkyl having up to 8 carbon atoms, cycloalkyl having 3 to 7 carbon atoms, aralkyl which is optionally substituted and has 1 or 2 carbon atoms in the alkyl moiety and 6 to 10 carbon atoms in the aryl moiety, and aryl which is optionally substituted and has 6 to 10 carbon atoms, aryl substituents in each case independently being halogen, cyano, nitro, alkyl, alkoxy and alkylthio each having up to 4 carbon atoms, halogenoalkyl, halogenoalkoxy and halogenoalkylthio each having 1 or 2 carbon atoms and up to 5 identical or different halogen atoms, dioxyalkylene which is optionally substituted by halogen or lower alkyl and has 1 or 2 carbon atoms in the alkylene radical, phenoxy which is optionally substituted by halogen, lower alkyl and lower halogenoalkyl, and alkoxycarbonylalkyl and alkoxycarbonylalkenyl each having 1 or 2 carbon atoms in the alkoxy moiety and each having up to 2 carbon atoms in the alkyl or alkenyl moiety, $R^1$, $R^2$ and $R^3$ each independently is hydrogen or alkyl having up to 6 carbon atoms, and $R^4$ is alkyl having 1 to 6 carbon atoms excepting the compounds in which $R^1$ and $R^3$ are hydrogen $R^4$ is methyl, R is alkyl, phenyl or phenyl which is substituted by halogen and/or methyl, and $R^2$ is hydrogen or methyl.

2. A substituted tetrahydrothiopyran-3,5-dione-4-carboxamide according to claim 1, in which R is alkyl having up to 6 carbon atoms, cyclopentyl or cyclohexyl; or phenyl, benzyl or naphthyl, which are optionally monosubstituted to independently trisubstituted, substituents in each case being fluorine, chlorine, bromine, nitro, cyano, methyl, ethyl, n- and i-propyl, n-, i-, s- and t-butyl, methoxy, ethoxy, methylthio, trifluoromethyl, trifluoromethoxy, trifluoromethylthio, dioxymethylene, dioxyethylene, dioxytrifluorochloroethylene, 2-methoxy-carbonylvinyl, 2-ethoxycarbonylvinyl, and/or phenoxy which is itself optionally monosubstituted to trisubstituted by methyl, chlorine and/or trifluoromethyl, $R^1$, $R^2$ and $R^3$ each independently is hydrogen, methyl, ethyl, n- or i-propyl or n-, i-, s- or t-butyl, and $R^4$ is methyl, ethyl, n- or i-propyl, n-, i-, s- or t-butyl, excepting the compounds in which $R^1$ and $R^3$ are hydrogen, $R^4$ is methyl, R is alkyl, phenyl or phenyl which is substituted by halogen and/or methyl, and $R^2$ is hydrogen or methyl.

3. A compound according to claim 1, wherein such compound is 2-isopropyltetrahydrothiopyran-3,5-dione-4-[N-(3,4-dichlorophenyl)]-carboxamide of the formula

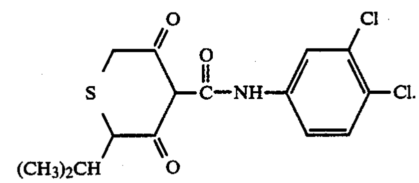

4. A compound according to claim 1, wherein such compound is 2,6-methyltetrahydrothiopyran-3,5-dione-4-(N-tert.-butyl)-carboxamide of the formula

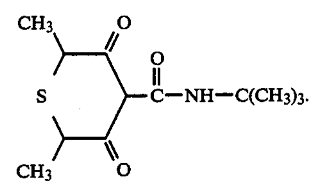

5. A compound according to claim 1, wherein such compound is 2,6-methyltetrahydrothiopyran-3,5-dione-4-(N-p-tolyl)-carboxamide of the formula

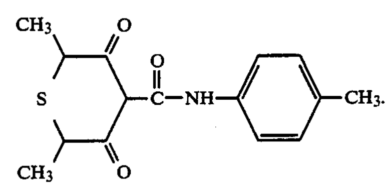

6. A compound according to claim 1, wherein such compound is 2,6-methyltetrahydrothiopyran-3,5-dione-4-[N-(3-trifluoromethylphenyl)]-carboxamide of the formula 7. A compound according to claim 1, wherein such compound is 2,6-methyltetrahydrothiopyran-3,5-dione-4-[N-(3-nitrophenyl)]-carboxamide of the formula

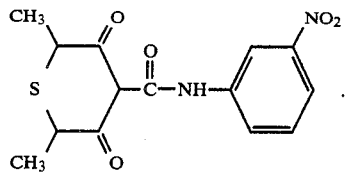

8. A compound according to claim 1, wherein such compound is 2,6-methyltetrahydrothiopyran-3,5-dione-4-[N-(4-chlorophenyl)]-carboxamide of the formula

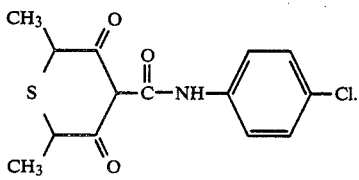

9. A compound according to claim 1, wherein such compound is 2,6-methyltetrahydrothiopyran-3,5-dione-4-[N-(3,4-dichlorophenyl)]-carboxamide of the formula

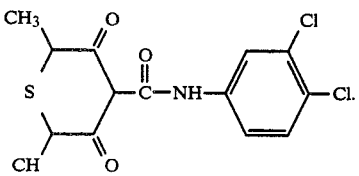

10. A compound according to claim 1, wherein such compound is 2,6-methyltetrahydrothiopyran-3,5-dione-4-[N-(3-chloro-4-trifluoromethylphenyl)]-carboxamide of the formula

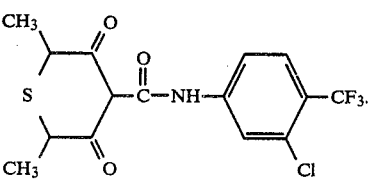

11. A compound according to claim 1, wherein such compound is 6-isopropyl-2-methyl-tetrahydrothiopyran-3,5-dione-4-[N-(4-chlorophenyl)]-carboxamide of the formula

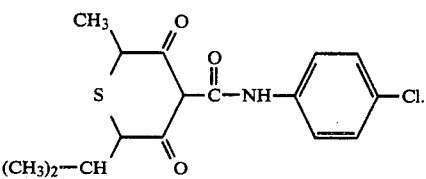

12. A compound according to claim 1, wherein such compound is 6-isopropyl-2-methyl-tetrahydrothiopyran-3,5-dione-4[N-(3,4-dichlorophenyl)]-carboxamide of the formula

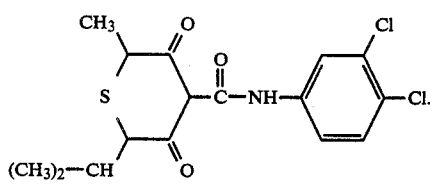

13. A fungicidal composition comprising a fungicidally effective amount of a compound according to claim 1 in admixture with a diluent.

14. A method of combatting fungi which comprises administering to such fungi or to a fungus habitat a fungicidally effective amount of a compound according to claim 1.

15. The method according to claim 14, wherein such compound is
2-isopropyltetrahydrothiopyran-3,5-dione-4-[N-3,4-dichlorophenyl)]-carboxamide,
2,6-methyltetrahydrothiopyran-3,5-dione-4-(N-tert.-butyl)-carboxamide,
2,6-methyltetrahydrothiopyran-3,5-dione-4-(N-p-tolyl)-carboxamide,
2,6-methyltetrahydrothiopyran-3,5-dione-4-[N-(3-trifluoromethylphenyl)]-carboxamide,
2,6-methyltetrahydrothiopyran-3,5-dione-4-[N-(3-nitrophenyl)]-carboxamide,
2,6-methyltetrahydrothiopyran-3,5-dione-4-[N-(4-chlorophenyl)]-carboxamide,
2,6-methyltetrahydrothiopyran-3,5-dione-4-[N-(3,4-dichlorophenyl)]-carboxamide,
2,6-methyltetrahydrothiopyran-3,5-dione-4-[N-(3-chloro-4-trifluoromethylphenyl)]-carboxamide,
2-isopropyl-6-methyl-tetrahydrothiopyran-3,5-dione-4-[N-(4-chlorophenyl)]-carboxamide or
2-isopropyl-6-methyl-tetrahydrothiopyran-3,5-dione-4-[N-3,4-dichlorophenyl)]-carboxamide.

16. A tetrahydrothiopyran-3,5-dione of the formula

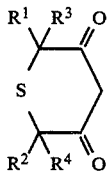

in which
$R^1$, $R^2$ and $R^3$ each independently is hydrogen or alkyl, and
$R^4$ is alkyl,
excepting the compounds in which
$R^1$ and $R^3$ are hydrogen,
$R^4$ is methyl or i-propyl, and
$R^2$ is hydrogen or methyl.

* * * * *